United States Patent
Daehne et al.

(10) Patent No.: US 9,717,274 B2
(45) Date of Patent: Aug. 1, 2017

(54) SMOKE-FREE CIGARETTE, CIGAR OR PIPE

(75) Inventors: Lars Daehne, Dahlwitz Hoppegarte (DE); Gabriella Egri, Berlin (DE); Heinrich Trescher, Worms (DE)

(73) Assignees: SURFLAY NANOTEC GMBH, Berlin (DE); SEVERUS PATENT AG, Rotkreuz (CH)

( * ) Notice: Subject to any disclaimer, the term of this patent is extended or adjusted under 35 U.S.C. 154(b) by 797 days.

(21) Appl. No.: 13/985,341

(22) PCT Filed: Feb. 17, 2012
(Under 37 CFR 1.47)

(86) PCT No.: PCT/EP2012/000727
§ 371 (c)(1),
(2), (4) Date: Feb. 26, 2014

(87) PCT Pub. No.: WO2012/110258
PCT Pub. Date: Aug. 23, 2012

(65) Prior Publication Data
US 2014/0246033 A1    Sep. 4, 2014

(30) Foreign Application Priority Data
Feb. 18, 2011    (DE) .......................... 10 2011 011 676

(51) Int. Cl.
| | |
|---|---|
| *A24F 47/00* | (2006.01) |
| *A24D 1/02* | (2006.01) |
| *A61M 15/00* | (2006.01) |
| *A61M 15/06* | (2006.01) |
| *A61M 16/10* | (2006.01) |

(52) U.S. Cl.
CPC .......... *A24F 47/008* (2013.01); *A24F 47/002* (2013.01); *A61M 15/0003* (2014.02); *A61M 15/0028* (2013.01); *A61M 15/06* (2013.01); *A61M 16/107* (2014.02); *A61M 2205/3613* (2013.01)

(58) Field of Classification Search
USPC .................................. 131/329, 347, 348, 360
See application file for complete search history.

(56) References Cited

U.S. PATENT DOCUMENTS

| | | | |
|---|---|---|---|
| 2008/0302374 A1 | 12/2008 | Wengert et al. | |
| 2013/0047984 A1* | 2/2013 | Dahne .................. | A61M 15/06 128/203.12 |

FOREIGN PATENT DOCUMENTS

| | | |
|---|---|---|
| DE | 102005034169 A1 | 2/2007 |
| DE | 10 2005 054 255 | 5/2007 |

(Continued)

OTHER PUBLICATIONS

German Office Action dated Feb. 1, 2012 from counterpart German App No. 102011011676.1.

*Primary Examiner* — Dennis Cordray
(74) *Attorney, Agent, or Firm* — Shuttleworth & Ingersoll, PLC; Timothy J. Klima

(57) ABSTRACT

The invention relates to a smokeless cigarette, cigar, or pipe having at least one depot (10) for storing and for defined release due to external heat input of nicotine and/or compound comprising nicotine to an airflow to be guided through the depot (10). According to the invention the depot (10) comprises at least one heat transfer segment (16) for targeted heat input for defined release of the nicotine and/or nicotine compound to the airflow.

11 Claims, 4 Drawing Sheets

(56) References Cited

FOREIGN PATENT DOCUMENTS

Figure 1:
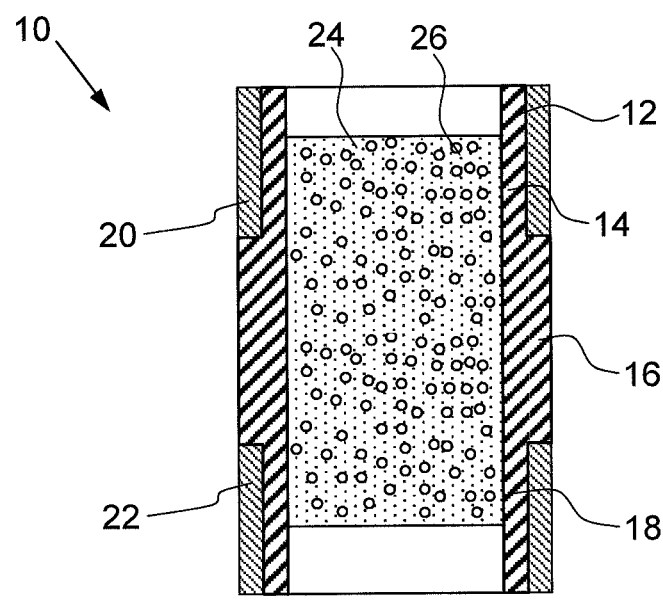

| DE | 102009015562 A1 | 10/2010 |
|----|-----------------|---------|
| EP | 0241698 | 10/1987 |
| EP | 0277519 | 8/1988 |

\* cited by examiner

SMOKE-FREE CIGARETTE, CIGAR OR PIPE

This application is the National Phase of International Application PCT/EP2012/000727 filed Feb. 17, 2012 which designated the U.S.

This application claims priority to German Patent Application No. DE102011011676.1 filed Feb. 18, 2011, which application is incorporated by reference herein.

The invention relates to a smokeless cigarette, cigar, or pipe having at least one depot for storage and defined release, induced by external application of heat, of nicotine and/or at least one compound comprising nicotine into an airstream flowing through the depot.

For some time, intensive attempts have been made to develop so-called smokeless cigarettes, cigars, or pipes, that is, devices for the targeted and defined release of nicotine and/or compounds comprising nicotine without tobacco being burned to produce smoke. The term "compound comprising nicotine" is understood in the present application to mean in particular nicotine salts, nicotine derivatives, and tobacco components comprising nicotine.

The products currently available on the market are problematic in that defined release of nicotine or the compound comprising nicotine is particularly often not ensured.

Electronic cigarettes are known wherein the indrawn airflow must be heated to a sufficiently high temperature prior to flowing through the depot for releasing the nicotine or compound comprising nicotine. A disadvantage of said known solution that the inertia of the overall system, that is, the reaction time from the first intake by the user until a sufficiently high temperature can be provided in the airflow in order to release the nicotine or compound comprising nicotine is too long to ensure sufficient and defined release of the nicotine or compound comprising nicotine from the depot. Furthermore, the amount of energy required to heat the airflow to a sufficiently high temperature, typically about 80° C., is so high that the required energy stores, such as rechargeable batteries, are rapidly depleted and no longer work properly due to the high amounts of energy after just a few charging cycles.

Based on this prior art, the object of the invention is to provide a smokeless cigarette, cigar, or pipe wherein the nicotine and/or the at least one compound comprising nicotine is released from the depot in a very targeted manner.

The object is achieved by a smokeless cigarette having features as described herein and particularly in that the depot comprises at least one heat transfer segment for targeted introduction of heat for the defined release of nicotine and/or the compound comprising nicotine into the airflow.

In the smokeless cigarette according to the invention, the depot of the cigarette has a heat transfer segment. Heat is fed into the interior of the depot from outside in a targeted manner by means of the heat transfer segment in order to bring about defined and uniform release of the nicotine or the compound comprising nicotine from the depot. Due to the provision of the heat transfer segment, the amount of energy required for releasing the nicotine or the compound comprising nicotine is also very low in comparison with the solutions known from the prior art. The heat transfer takes place by heat conduction or heat radiation directly from outside into the depot, thus minimizes the occurrence of heat losses. The heat transfer segment is thereby preferably conceived so that the heat input to the heat transfer segment is distributed uniformly in the depot.

Advantageous refinements of the invention will be apparent from the present description, claims and figures.

In a particularly preferred embodiment of the smokeless cigarette according to the invention, the depot comprises a sleeve at least partially enclosing the depot and made of a material having high thermal conductivity for targeted heat input. The sleeve, typically at least partially open at both ends, thereby serves for protecting the depot itself. The depot is thereby either securely integrated in the sleeve, or the sleeve is subsequently slid over the depot. In any case, good external heat transfer through the sleeve to the depot must be ensured. The sleeve preferably has a round, hollow cylindrical interior shape, while the exterior can optionally be round, oval, or polygonal in shape. A stepped design of the exterior surface of the sleeve is also possible. It is particularly advantageous if the heat transfer segment of the sleeve making contact with the depot at the interior wall extends over the entire axial length of the depot while the exterior of the sleeve is made of the heat transfer material only in the area interacting with the external heat source.

In a further preferred embodiment, the heat transfer area is located in the interior of the depot, wherein the exterior sleeve is made of a material as heat insulating as possible. The depot in this case preferably has a recess that can have a different geometric shape, such as cylinder, slit, rectangle, or sphere. A heating element made of a material having high thermal conductivity and heated by introducing external energy, such as electrical current, protrudes into said recess. For the segment of the sleeve or element transferring the heat, it is proposed that a material having relatively high thermal conductivity is used. A material having a thermal conductivity in a range from 30 to 450 W/(m·K) is thus suitable. Preferably a material having a thermal conductivity in a range from 85 to 300 W/(m·K) is used, particularly preferably in a range from 185 to 250 W/(m·K). Aluminum, copper, iron, or alloys of said components are particularly well suited as materials for this segment of the sleeve transferring heat. If the sleeve is made only partially of said material, the segment not intended for heat transfer can also be made of an insulating material in order to prevent undesired heat dissipation.

In the search for a suitable material for the depot itself, a surprising result was that hybrid structures, that is, structures made of different materials comprising a hierarchy of porosities, are particularly well suited for storing the nicotine and/or compounds comprising nicotine as well as optional flavoring agents on one hand, and for releasing the same in sufficient amounts when heat is applied appropriately. The hybrid structure further acts as a type of filter.

In a particularly preferred embodiment of the smokeless cigarette, the depot comprises a hybrid structure made of an open-pore, macroporous support matrix through which the air can flow, while nanopores provided in the support matrix serve for storing and releasing the nicotine and/or the compounds comprising nicotine and optionally additional favoring agents.

Attempts at long-term stability of nicotine in the described depot, in comparison with carrier materials typically in use, such as acetate fibers, resulted in significantly reduced yellow or brown coloring. The nicotine present in nanoporous particles is more stable, in comparison with nicotine in an absorbent carrier such as acetate fibers, with respect to oxidation in air. This is notable because the contact surface area to the air provided by the nanoporous particles is very large. It is suspected, without being accepted as a limitation, that the oxidation sensitivity of nicotine is significantly reduced after adsorption to the surface of the nanoporous material, such as the inner and outer surface of silica particles.

The support matrix is advantageously made of particles or fibers permanently bonded to each other, while the nanopores are implemented in nanoporous particles held immobile in the support matrix. The nanoporous particles in this solution are preferably made of a different material than the support matrix.

According to a preferred embodiment the nanoporous particles are mixed together with the particulate material (microparticles, fibers, or the like) and then the particulate material is bonded together to form an open-pore support matrix, wherein the nanoporous particles are thereby simultaneously immobilized in or on the support matrix.

The nanoporous particles particularly preferably comprise a higher melting temperature in comparison with the material of which the support matrix is made, or in comparison to the particles from which the support matrix is formed. It is thus ensured that the nanoporous particles do not melt or clog the pores when the support matrix is thermally treated in order to solidify the support matrix. The nanoporous particles can thus be "embedded" in the surface of the support matrix particles when melted.

A particular advantage of the nanoporous particles being permanently attached by sintering to the surface of a macroporous support matrix and having high specific surface area and affinity for active and flavoring substances and the use thereof in a depot for releasing substances into the permeating air is that only the particular previously bonded substances are released. In addition to the active and/or flavoring substances present in gaseous form, preferably no liquid droplets of any ancillary substances or large quantities of particles hazardous to health are present in the airflow exiting the depot. Fixing the nanoporous particles on the macroporous support matrix prevent the nanoporous particles from being able to be carried along in the air flow.

Alternatively or additionally, the support matrix can also be made substantially of an inorganic material such as glass, silicates, or aluminum silicates, while the nanopores are formed in the material of the support matrix itself.

The quantity and the size of the nanoporous particles are selected so that the macropores cannot be clogged and that sufficient active substance can be adsorbed in the interior of the particles. The nicotine or compound comprising nicotine is adsorbed, for example, and present in the interior of the nanoporous particles. In particular, the nicotine or compound comprising nicotine and any added flavoring agents can be present directly in the nanopores, that is, without being dissolved in a solvent.

The support matrix is preferably constructed from particles, fibers, particulate material, or mixtures of said materials. The particulate material or mixture of materials can be sintered, fused, glued, or otherwise bonded to each other so that a mechanically stable, open-pored support matrix results.

The nanoporous particles can be fixed on the surface of the macroporous support matrix formed by sintering, for example, so that the nanopores of the fixed particle are not enclosed on the side thereof facing away from the surface of the support matrix. When filling the depot, as well, the pores are prevented from being closed off.

Alternatively, the support matrix can also be made of a loose fill of particulate material or a material mixture, wherein the support matrix is present in a suitable container of the depot on which the at least one heat transfer segment is implemented.

The release of the substances bonded or adsorbed in the hybrid structure into the airflow takes place preferably by means of convection and/or diffusion. The preferred structural features of the depot, such as the support matrix, can be determined from the preferred release rates of the substances present in the depot for the specific application.

The scope of the invention further relates to implementing the depot such that the hybrid structure is formed from an open-pore macroporous support matrix having channels through which the airflow can easily flow, while the nanopores comprise the active substance to be released. The channels comprise an average width, for example, that altogether permit permeation of the airflow. For example, the channel width can be in a range of a few hundred micrometers, such as between 100 μm and 800 μm. It is, however, self-evident that said description refers to an average channel width, because the channels are irregular in form and can also comprise a distribution of channel widths.

The microparticles of the depot used for forming the support matrix comprises sizes from 200 to 1000 μm. The nanoporous particles are permanently fixed to the surface of the support matrix, for example by sintering. It is thereby conceivable that the open-pore support matrix comprises macropores that are greater than the nanoporous particles used for receiving the nicotine or compound comprising nicotine. The size of the macropores present in the support matrix is then typically in a range between 10 μm and 800 μm, such as between 20 μm and 700 μm, particularly between 25 μm and 600 μm. Said nanoporous particles preferably comprise average particle diameters of 5 μm to 500 μm, particularly preferably diameters between 10 μm and 300 μm, and particularly preferably diameters between 20 μm and 150 μm. The nanopores are typically in a range between 1 nm and 900 nm. The pore diameter is, for example, in a range between 3 nm and 700 nm, preferably in a range between 6 nm and 500 nm.

In various embodiments particle or fiber sinter materials made of inorganic materials such as silicates or aluminum silicates are used for forming the macroporous support matrix of the depot. Organic polymers, such as polyethylene or polypropylene, polyvinylchloride, polycarbonate, polyurethane, polyester, and other materials can likewise be used for the macroporous support matrix. Due to the use of the depot for cigarettes, cigars, or pipes, care should be taken that no plasticizers are present in the polymers. In the case of particulate sinter materials, the particles size should be adapted so that the air can easily flow through the desired length of the depot.

The depot can also be formed by a mixture of support particles or fibers of different sizes, or of particles of different materials. Various nanoporous particles differing in size and/or shape and/or pore size and/or material and/or affinity to the active substance can likewise be embedded in the support matrix. The particles used for producing the depot can likewise be a mixture of porous particles charged differently or charged with different substances.

The size and the shape of the depot are adapted to the particular application. It is particularly adapted to the geometric conditions of the cigarette, cigar, or pipe. For example, the depot can be designed as a disposable depot to be stored in the head or stem or a conventional tobacco pipe or may have the size, shape, and color of a cigarette filter or be arranged for use in an imitation of a cigar or a cigarillo.

The adaptation provides good access to the nanopores for the permeating airflow and uniform distribution of the substance stored in the depot. The shape of the depot and/or of the cartridge can thereby advantageously be cylindrical or even polygonal, such as cubic or cuboid. According to one or more embodiments a replacement filter stick for a smokeless cigarette comprises the depot.

Depending on the intended use, the length and width or diameter of the macroporous support matrix is suitably selected as a function of the volatility of the active substance, the temperature of the incoming airflow, the desired concentration of nicotine in the airflow exiting the depot, the amount of charge, the flow resistance, and the amount of nanoporous particles to be immobilized.

Surprisingly, inorganic adsorbent materials having as great an inner surface area as possible are well suited as nanoporous depot materials for the nicotine or compounds comprising nicotine and optionally stored active substances and flavoring agents. The inner surface of the adsorbent materials is formed by the walls, so that a large contact surface area is available for pore-entering substances. In addition to porous aluminum silicates, nanoporous silicates are particularly well suited for receiving nicotine and flavoring agents.

Said adsorbent materials comprise an open-pore network of interconnected tubes. They are commercially available as chromatographic carrier materials with defined average pore widths, typically of 3 nm, 7 nm, 12 nm, 30 nm, and 100 nm. Wider pore distributions in the nanometer range, such as 3 nm to 700 nm, are also possible.

The particle size of suitable nanoporous materials is 10 µm to 1 mm, particularly from 50 µm to 700 µm, for example. The nanoporous materials can comprise a spherical shape. According to a particularly preferred embodiment irregularly broken materials and thus irregularly formed particles are used for embedding.

In one embodiment, the smokeless cigarette, cigar, or pipe comprises two or more depots that are combined with each other and in which various substances are adsorbed. At least one of the depots is thereby equipped with a heat transfer segment. For example, one of the substances can serve for partially or completely modifying, such as chemically converting, the other substance. For example, when using nicotine, an additional depot is positioned ahead of the depot having nicotine, in which an acid is stored that converts the nicotine at least partially into a nicotine salt in order to improve the tolerability of the inhaled nicotine. The acid is therefore present in the "upstream" depot.

In addition to high adsorption capacity for polar active substances such as nicotine, the nanoporous materials also have an affinity for less polar materials such as flavoring agents or essential oils. Such flavoring agents can be adsorbed separately or simultaneously with the substance such as nicotine and released in addition. Of particular interest in this context are terpenes and terpenoids, particularly mono and sesquiterpenes and essential oils or solids such as mountain pine oil, eucalyptus oil, peppermint oil, clove oil, tobacco aroma oil, or menthol.

Combinations of active substances having aromas that are preferred or vital to the particular application can thereby be delivered to the airflow. For example, they can provide a characteristic flavor to the indrawn airflow.

One or more further embodiments of the invention relate to storing various active, flavoring, or ancillary agents that have a negative effect when released together in separate sequentially arranged hybrid depots through which the air flows.

The method steps for producing a depot described here for active substances and/or flavoring agents according to one or more embodiments comprise selecting a microparticulate matrix for embedding nanoporous particulate material, selecting a nanoporous particulate material, selectively adjusting the affinity of the nanoparticulate material by modifying the same, co-sintering the nanoporous material and the support material at a temperature near the melting or softening temperature of the material used as the support matrix, and adsorbing active substances and/or flavoring agents on the surface of the nanoporous of the nanoporous material. Selective adjustment of the adsorbed quantity of active substance can thus take place.

Inorganic materials such as glass, silicates, or alumosilicates or thermoplastic organic polymers can be used as the matrix for fixing the nanoporous particles.

According to one or more embodiments, the step of selectively adjusting the affinity for active substances or flavoring agents can be eliminated when selecting the nanoporous particulate material. As explained above, the method steps of co-sintering and adsorbing or charging can also be combined with each other.

Nanoporous materials made of silicon dioxide or alumosilicates are currently produced in a wide range of embodiments.

The following criteria can be used when selecting for the described depot.

1. Charge Capacity

For the lowest possible volume of the depot, a high charge capacity of the nanoporous materials is desired. The charge capacity is indicated here as a percentage by mass of active substance (such as the mass of nicotine) per mass of the filled particle. Suitable charge capacities are between 20% and 90%, such as between 30% and 85%, particularly between 60% and 80%.

2. Releaseability

In materials having very high affinity to nicotine or to the compound comprising nicotine the distribution coefficient between the air and the surface is shifted greatly toward the latter. As a result, the equilibrium concentration of the nicotine or compound comprising nicotine in the air is very low. In this respect the affinity to nicotine or to the compound comprising nicotine should be just sufficient to ensure effective adsorption. Precoating the nanoporous particles with polyelectrolytes by means of the LbL technique is proposed for adjusting the interactions between the pore surface and nicotine or a compound comprising nicotine that determine the affinity. Depending on the active substance, the complementary polyelectrolyte should be selected so that a cationic, anionic, hydrogen bridge bonding, or hydrophobic surface is presented.

3. Size of the Nanoporous Particles

This parameter substantially determines the design of the depot filter. If the size of the nanoporous particles is too small, they can be carried off if insufficiently fixed and filtered and escape from the depot, and enter the respiratory tract of the inhaling person, for example. If the particles are too large, then the exchange of air with the active substance, such as nicotine, in the interior of the particle is insufficient and the macropores of the matrix become clogged. Suitable size distributions for the nanoporous particles are 10 μm to 1 mm, particularly from 50 μm to 700 μm, for example. Irregular particles having a tight size distribution are particularly suitable.

4. Pore Width

The pore width of the nanoporous particles determines the available surface area and thus the amount of adsorbed nicotine, adsorbed compound comprising nicotine, or adsorbed flavoring agent, as well as the rate of the air exchange. While lower pore widths lead to higher charge capacity, such as for nicotine, the diffusive air exchange is reduced at the same time. For use in a depot, it has been found to be advantageous to use materials having pore distribution that is not too tight. Pore diameters having a wide distribution from 1 nm to 900 nm, particularly in the range of 3 nm to 700 nm, are suitable for effective adsorption. The internal surface area, measured by BET nitrogen adsorption, should be 30-1000 $m^2/g$, preferably 100-600 $m^2/g$.

5. Fixing the Nanoporous Particles in the Macroporous Matrix

In order to allow uniform impingement of the nanoporous particles comprising the nicotine and/or compound comprising nicotine by the permeating air, but to prevent the escape of the particles into optionally inhaled air, the particles should be stably fixed in the depot. An advantageous embodiment of a depot implements co-sintering of the nanoporous particles that melt only at higher temperatures with larger sinter granulates made of polymers that have a lower melting or softening point. The proportion of nanoporous particles in the sintered piece can be between 2% and 40%, such as between 5% and 20%. The proportion of nanoporous particles should be selected so that the sintered or melted support matrix is still sufficiently mechanically stable. For example, proportions of nanoporous particles greater than 40% can no longer ensure the integrity of the macroporous support matrix in some cases.

The contact surface to the adsorbed active substance provided by the nanoporous particles on the microporous support matrix for the permeating air is very large in comparison with the contact surface of the fluid-filled capillary absorbent materials typically in use. While the latter has only the accessible cross section (meniscus) of the filled capillary as an evaporation surface, the gas exchange in the case of the described depot takes place over the entire surface area thereof comprising the adsorbed active substance.

Tests of the adsorption of nitrogen molecules at the surface of such nanoporous materials according to the typical BET method indicate that the inner surface area can be greater than 270 $m^2/g$.

According to one or more embodiments the nanoporous particles are not filled by dripping pure liquid nicotine. Filling takes place by dissolving the active substance in a suitable organic solvent, for example a volatile solvent, leaving the active substance behind in the depot after evaporating completely For example, pentane, hexane, heptane, acetone, ethanol, methanol, or other volatile organic solvents may be used as the solvent. After the solvent evaporates, the active substance is adsorptively bonded as desired to the internal surface of the nanoporous particles without significantly preventing air entry. The active substance is also present on the external surface of the particles, wherein the internal surface provided by the nanopores is substantially larger than the external surface of the particles and the support matrix.

Nanoporous materials having a suitable affinity (the pore surface) to the active substance (flavoring agent) and the addition of a quantity of active substance (quantity of flavoring agent) according to the charge or adsorption capacity of the nanoporous material thus allow a high level of charge of the depot with nicotine and/or flavoring agents as well as rapid release of the same into a passing or permeating airflow. The gas transport in the interior of the porous particles can thereby take place predominately by diffusion.

In order to selectively modify the affinity of the nanoporous materials in the direction of optimal acceptance as well as release, various potential pretreatments of the pore surfaces have been investigated using the example of a preliminary cleaning, activation, etching with acids or bases, and silanization.

Simple coating of the pores with polyelectrolytes using the layer-by-layer (LbL) technique surprisingly proved to be particularly suitable for controlling the acceptance and release of active substances. The LbL coating of nanopores for the purpose of fictionalization is disclosed in patent application DE 10 2004 013 637. For example it is possible to delay the release of active substances by means of such a modification using polyelectrolyte coatings.

One or more embodiments use the temperature dependence of the adsorption equilibrium of the active substances or flavoring agents on nanoporous particles. Depending on the requirements of the particular application this can be controlled in addition to adjusting the affinity of the surface of the nanoporous particles for the active substances or flavoring agents by means of the temperature of the depot and/or by means of the temperature of the gas or gas mixture permeating the depot itself.

In addition to the nicotine and/or the compound comprising nicotine, at least one flavoring agent is preferably stored in the depot of the smokeless cigarette, cigar, or pipe and is likewise released when heat is input.

Figure 2:
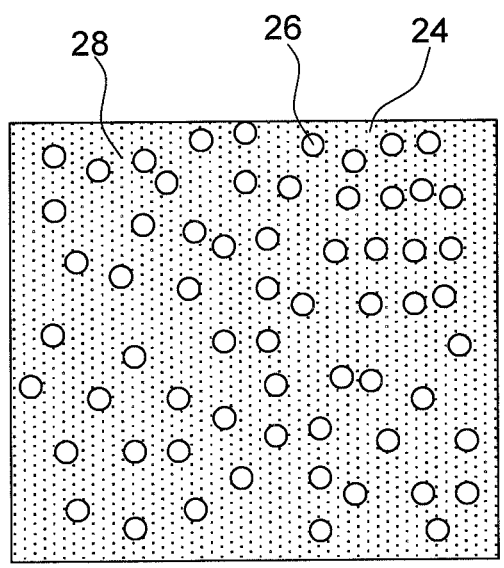
Figure 3:
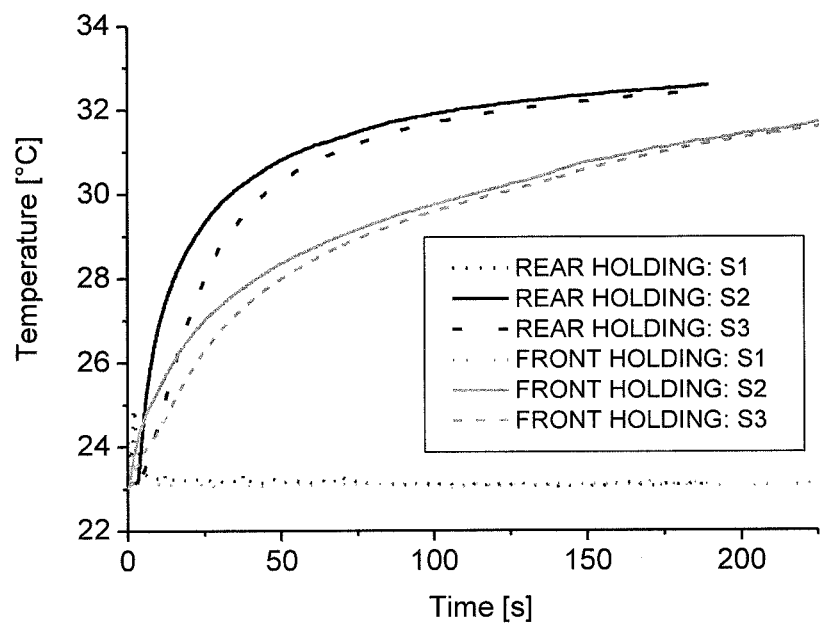
Figure 4:
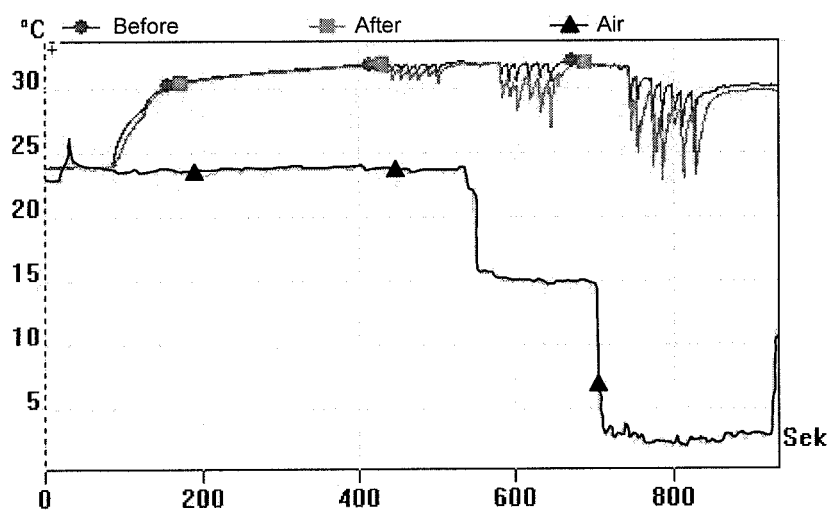
Figure 5:
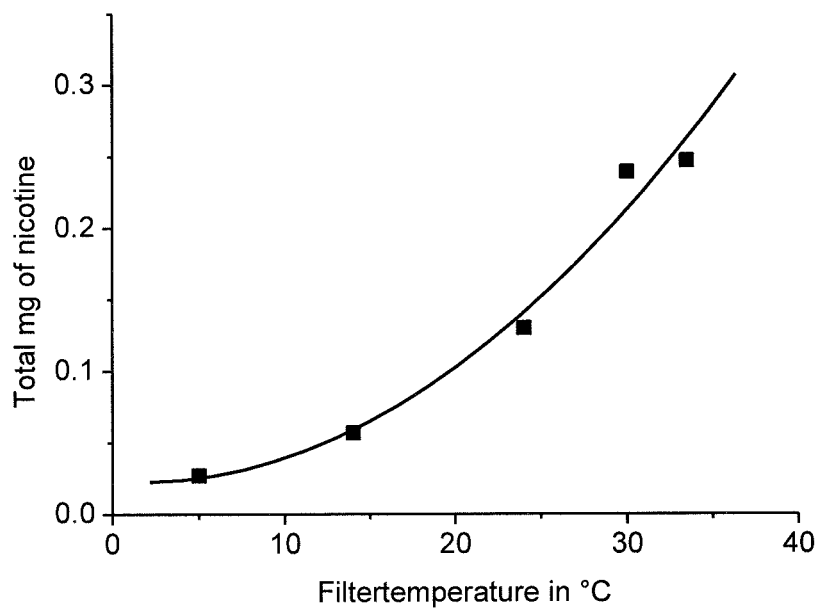
Figure 6:
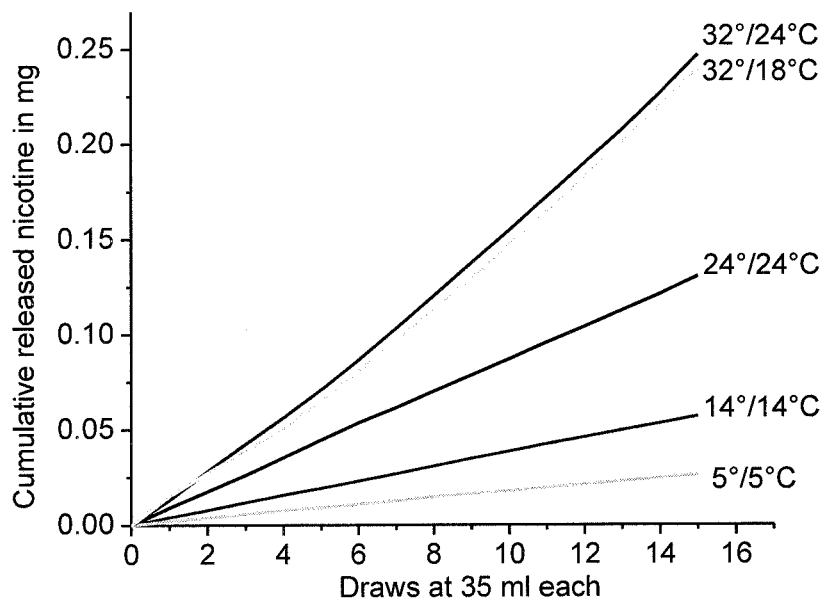
Figure 7:
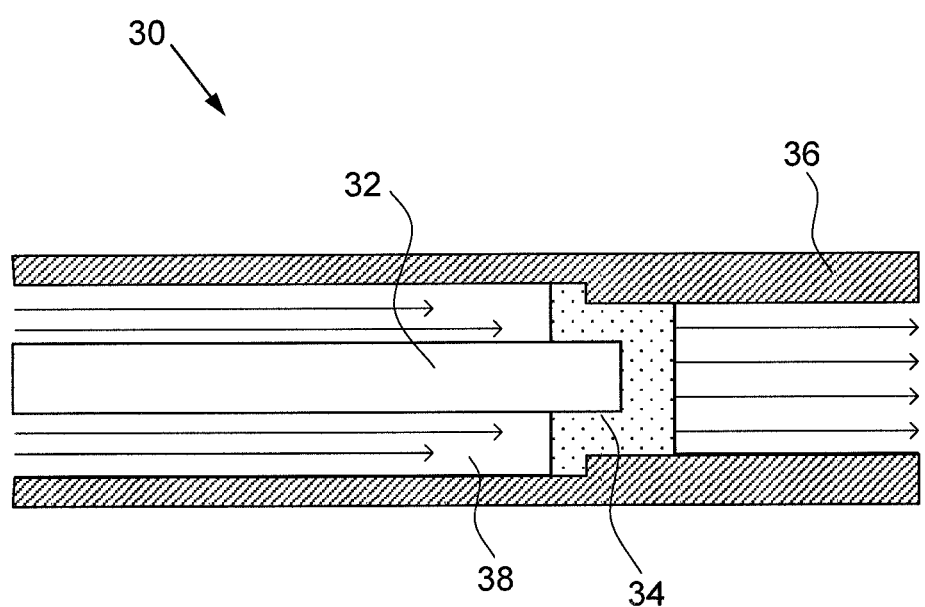

The invention is explained in more detail below using two embodiments and referencing the drawing. They show:

FIG. 1 A section view through a first embodiment example of a depot according to the invention, having a sleeve for a smokeless cigarette, FIG. 2 Schematic construction of the depot according to FIG. 1;

FIG. 3 A heating curve relative to time for a depot having a sleeve made of aluminum, FIG. 4 A temperature curve when "smoking" the depot for drawing behavior typical of a smoker and a sleeve having a high heat capacity;

FIG. 5 Release of nicotine from the depot filter as a function of temperature;

FIG. 6 Release of nicotine from a depot according to the invention according to FIG. 1 as a function of the number of draws (each 35 ml) at different temperatures of the filter, and FIG. 7 A section view through a second embodiment example of a depot according to the invention, having a sleeve and inserted in a smokeless cigarette, FIG. 1 shows a section view of a depot 10 for storing and releasing nicotine for a smokeless cigarette not shown in greater detail. The depot 10 has a sleeve 12 made of aluminum and having a constant internal diameter. The shell of the sleeve 12 is stepped in design and has a first segment 14 having a smaller external diameter, a second segment having a larger external diameter and serving as a heat transfer segment 16, and a third segment 18 adjacent thereto and having a smaller external diameter. The first and third segments 14 and 18 of the sleeve 12 are each enclosed by a thermally insulating paper wrapper 20 and 22 and have on one side a mouthpiece made of a suitable material and not shown in further detail. A macroporous support matrix 24 is received in the interior of the sleeve 12, in which a plurality of nanoporous particles 26 is embedded.

The average draw volume of 35 ml and the draw time of an average smoker of 1 to 2 second result in a very brief contact period between the air permeating the depot 10 and the nicotine reservoir. The transition of nicotine into the gas phase correlates approximately with the contact area between the nicotine reservoir and the air.

The depot 10 shown is received in a housing of the smokeless cigarette so that the heat transfer segment 16 is directly or indirectly in contact with the hand of the user when the cigarette is held. The heat of the hand is then transferred to the heat transfer segment 16, which in turn conducts the heat inward to the support matrix 24. By heating the support matrix 24 the release rate of the nicotine and the flavoring agents is increased, so that a sufficient quantity of nicotine and flavoring agents can be consumed by the user with every draw. The two paper wrappings 20 and 22 thereby prevent heat radiation to the outside, so that the support matrix 24 remains uniformly heated.

The volume of the sleeve 12 according to FIG. 1 is adapted to the wall thickness thereof so that the heating time after positioning between the fingers runs as quickly as possible.

FIG. 2 shows the schematic construction of the support matrix 24 of the depot 10 for storing nicotine and flavoring agents. The support matrix 24 is a macroporous support matrix 24 formed from sintered particles. Pores, caverns, and intermediate spaces 28 are implemented in the support matrix 24 and remain intact after sintering. The caverns and intermediate spaces 28 are thereby implemented so that the support matrix 24 comprises a defined draw resistance for an airflow to be drawn in by a user.

The pores, caverns, and intermediate spaces 28 form a continuous network in which the nanoporous particles 26 are stably and permanently adhered or embedded. The nanoporous particles 26 comprise pores in the range of 1 nm to 900 nm. The nicotine and optionally compounds comprising nicotine and the flavoring agents are adsorbed on the surface of the nanoporous particles 26, particularly on the interior surfaces thereof formed by the pore walls, and are in continuous exchange with the air flowing through the support matrix when air is drawn in through the depot 10.

The depot 10 described here can both ensure sufficient nicotine release to the breathing air and protect the nicotine against oxidation.

The temperature curve of a depot 10 having a sleeve 12 made of aluminum having a wall thickness of 1 mm (top/bottom) or 1.5 mm at the finger contact surface, and of the depot after being picked up and enclosed in the fingers at 23° C. air temperature. The position of the sleeve 12 between the fingers is thereby preferably such that the contact surface when held between the second phalanges as viewed from the fingertip (front holding) between the index and middle fingers is less than between the third phalanges (rear holding). As the volume of the sleeve 12 decreases, the heat capacity is lower and the heating takes place more rapidly as well. The wall thickness of the sleeve 12 should thus advantageously be between 0.2 and 2.5 mm, very particularly preferably between 0.4 and 1.5 mm.

FIG. 3 thereby shows heating curves for the sleeve 12 made of aluminum (wall thickness 1/1.5 mm) due to the finger when held between the index and middle fingers. In the diagram, the label "Front holding" means holding the sleeve 12 between the second phalanges as seen from the fingertip, "Rear holding" means holding the sleeve 12 between the third phalanges, "S1" means the ambient temperature, "S2" means the temperature of the sleeve 12, and "S3" means the temperature at the center of the depot.

The heat capacity of the heated sleeve 12 must in turn be sufficient to compensate for the cooling of the filter by the permeating air volume of 35 to 50 ml when drawing heavily in cold air. Measurements of the sleeve and filter temperature at the outlet of the depot 10 were taken at various air temperatures.

FIG. 4 shows the temperature curve of the depot 10 when "smoking" for a draw behavior typical of a smoker and a sleeve 12 having high heat capacity. It is clearly evident that the temperature drops off more severely at the filter depot than at the sleeve, but that it recovers quickly due to the supply of heat through the sleeve 12. Even at an air temperature of only 3° C. the temperature at the outlet of the depot 10 does not fall below 23° C. For sleeves 12 having lower heat capacity the temperature drops become more severe and the recovery times to reach the outlet temperature become longer, especially when the exterior air is cold.

The temperature functions shown in FIG. 4 correspond to the ambient (air) temperature, the heat transfer sleeve 12 before the air inlet, and the depot 10 after the center at the air outlet for typical inhalation at different temperatures by a smoker.

The measured values of the total nicotine release when smoking a cold cigarette and the finger cigarette (at 24° C. air temperature) and the factor of improvement due to the cigarette according to the invention are listed in the following table:

| Filter temperature in ° C. | Nicotine yield for 15 draws of 35 ml according to DIN . . . | Factor of increase of nicotine yield for finger heating relative to a cold cigarette |
| --- | --- | --- |
| 32 | 0.25 | 1 |
| 24 | 0.13 | 1.9 |
| 14 | 0.056 | 4.5 |
| 5 | 0.026 | 9.6 |

The release of nicotine from the depot 10 is shown in FIG. 5 as a function of the temperature of the depot, while FIG. 6 shows the release of nicotine from the depot 10 as a function of the number of draws (of 35 ml each) at different temperatures of the depot 10 (left number on the curves) and the indrawn air (right number). As can be seen, the nicotine release for a finger cigarette is barely influenced by the ambient temperature, but for a cigarette without a heat transfer surface it falls off severely as the temperature drops.

FIG. 7 shows a second embodiment example of a depot 30 having a heat source 32 comprising an external energy input.

For said second embodiment example the heat source 32 is disposed so that it interacts with a heat transfer segment 34 in the interior of the depot 30 for transferring heat (comment: the arrow in the drawing is not aligned precisely with the depot.) The sleeve 36 is thereby made of a material having higher thermal insulation, while the depot 30 is constructed in the manner described above. The heat source 32 is introduced into a recess in the depot 30 with a precise fit, said heat source having the form of a bar having high thermal conductivity and transferring heat to the depot 30. The indrawn air 38 is already slightly preheated and passes through the heated depot 30 and is largely saturated with nicotine as it exits the depot toward the mouth.

LIST OF REFERENCE NUMERALS

10 depot
12 sleeve having high thermal conductivity
14 first segment having smaller outer diameter
16 heat transfer segment
18 third segment having smaller outer diameter
20 paper wrapper
22 paper wrapper having a mouthpiece
24 macroporous support matrix
26 nanoporous particles
28 caverns and intermediate spaces
30 depot
32 heating source 34 heat transfer segment
36 insulating sleeve
38 preheated air

The invention claimed is:

1. A smokeless cigarette, cigar, or pipe comprising:
a depot for storage and defined release of at least one chosen from nicotine and a compound comprising nicotine into an airstream flowing through the depot, the defined release induced by application of heat external to the depot by a hand of a user,
the depot comprising:
a hybrid structure made of an open-pore macroporous support matrix through which the airstream flows,
nanopores provided in the support matrix for storing and releasing the at least one chosen from nicotine and the compound comprising nicotine,
a sleeve including:
an interior in which the support matrix is positioned, and
a heat transfer segment for transferring the application of the heat external to the depot by the hand of the user into the nanopores for the defined release of the at least one chosen from nicotine and the compound comprising nicotine from the nanopores into the airstream flowing through the depot.

2. The smokeless cigarette, cigar, or pipe according to claim 1, wherein a length of the heat transfer segment is dimensioned to provide sufficient heat transfer into the nanopores from two human fingers of one hand to release the at least one chosen from nicotine and the compound comprising nicotine from the nanopores.

3. The smokeless cigarette, cigar, or pipe according to claim 1, wherein a thermal conductivity of a material of the heat transfer segment is in a range from 30 to 450 W/(m·K).

4. The smokeless cigarette, cigar, or pipe according to claim 1, wherein the support matrix is made of particles or fibers permanently bonded to each other and the nanopores are implemented in nanoporous particles held immobile in the support matrix.

5. The smokeless cigarette, cigar, or pipe according to claim 4, wherein the nanoporous particles are made of a different material than the support matrix.

6. The smokeless cigarette, cigar, or pipe according to claim 1, wherein the support matrix is substantially made of at least one inorganic material chosen from glass, silicates, and alumosilicates, and the nanopores are implemented in the material of the support matrix.

7. The smokeless cigarette, cigar, or pipe according to claim 1, wherein a flavoring agent is stored in the depot in addition to the at least one chosen from nicotine and the compound comprising nicotine and the flavoring agent is released when heat is input.

8. The smokeless cigarette, cigar, or pipe according to claim 1, and further comprising a base body in which the depot implemented as a disposable item is received.

9. The smokeless cigarette, cigar, or pipe according to claim 1, wherein a thermal conductivity of a material of the heat transfer segment is in a range from 85 to 300 W/(m·K).

10. The smokeless cigarette, cigar, or pipe according to claim 1, wherein a thermal conductivity of a material of the heat transfer segment is in a range from 185 to 250 W/(m·K).

11. The smokeless cigarette, cigar, or pipe according to claim 1, wherein the heat transfer segment includes an exposed external portion for direct contact with the hand of the user.

* * * * *